(12) United States Patent
Haase (10) Patent No.: US 7,867,221 B2
(45) Date of Patent: Jan. 11, 2011

(54) INFUSION DEVICE AND OVERFILL PROTECTION MECHANISM FOR USE WITH SAME

(75) Inventor: James Martin Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1266 days.

(21) Appl. No.: 11/412,375

(22) Filed: Apr. 27, 2006

(65) Prior Publication Data

US 2007/0255260 A1 Nov. 1, 2007

(51) Int. Cl.
A61M 37/00 (2006.01)
A61M 31/00 (2006.01)
A61K 9/22 (2006.01)

(52) U.S. Cl. .............. 604/891.1; 604/132; 604/288.02

(58) Field of Classification Search .............. 604/891.1, 604/890.1, 892.1, 93.01, 131, 151, 288.01–288.04, 604/204, 132

See application file for complete search history.

(56) References Cited

U.S. PATENT DOCUMENTS

| | | | | |
|---|---|---|---|---|
| 4,077,405 | A | * | 3/1978 | Haerten et al. ............. 604/66 |
| 4,360,019 | A | | 11/1982 | Portner et al. |
| 4,373,527 | A | * | 2/1983 | Fischell .............. 604/891.1 |
| 4,573,994 | A | * | 3/1986 | Fischell et al. .......... 604/891.1 |
| 4,692,147 | A | | 9/1987 | Duggan |
| 4,714,462 | A | * | 12/1987 | DiDomenico ............. 604/67 |
| 4,772,263 | A | | 9/1988 | Dorman et al. |
| 5,158,547 | A | * | 10/1992 | Doan et al. ............ 604/288.01 |
| 5,242,406 | A | * | 9/1993 | Gross et al. ............. 604/132 |
| 5,507,737 | A | | 4/1996 | Palmskog |
| 5,665,070 | A | | 9/1997 | McPhee |
| 5,725,017 | A | | 3/1998 | Elsberry et al. |
| 6,152,898 | A | * | 11/2000 | Olsen .................. 604/93.01 |
| 6,210,368 | B1 | | 4/2001 | Rogers |
| 6,228,050 | B1 | * | 5/2001 | Olsen et al. ............. 604/93.01 |
| 6,482,177 | B1 | | 11/2002 | Leinders |
| 6,488,652 | B1 | | 12/2002 | Weijand et al. |
| 6,542,350 | B1 | | 4/2003 | Rogers |

(Continued)

FOREIGN PATENT DOCUMENTS

EP 1048309 A2 11/2000

(Continued)

OTHER PUBLICATIONS

"The Baxter Infusor, A guide for patients and their carers", Christie Hospital NHS Trust, Manchester, United Kingdom, May 2005; 12 pgs.

(Continued)

*Primary Examiner*—Matthew F Desanto
(74) *Attorney, Agent, or Firm*—Mueting, Raasch & Gebhardt, P.A.

(57) ABSTRACT

A medical device and displacement-based over-pressurization mechanism (OPM) for use with the same. The OPM may be positioned in or along a refill passageway of the device. It may include a valve plunger having a portion in biased, abutting contact with a reservoir surface that moves as the reservoir volume changes. The reservoir surface may move between a full position and a refill position. The OPM is preferably configured to close and occlude the refill passageway when the reservoir and reservoir surface reach the full position, e.g., before reaching an overfill position. A sensor may also be provided to detect a position of the valve plunger.

25 Claims, 5 Drawing Sheets

U.S. PATENT DOCUMENTS

| | | | |
|---|---|---|---|
| 6,554,822 | B1 | 4/2003 | Holschneider et al. |
| 6,572,583 | B1 | 6/2003 | Olsen et al. |
| 7,510,552 | B2 * | 3/2009 | Lebel et al. .............. 604/891.1 |
| 2002/0173773 | A1 | 11/2002 | Olsen |
| 2003/0216714 | A1 | 11/2003 | Gill |
| 2005/0024175 | A1 | 2/2005 | Gray et al. |

FOREIGN PATENT DOCUMENTS

| | | |
|---|---|---|
| EP | 1048309 A3 | 10/2001 |
| EP | 1 058 565 B1 | 5/2003 |
| EP | 1048309 B1 | 3/2007 |
| WO | WO 03/099351 A2 | 12/2003 |
| WO | WO 03/099351 A3 | 7/2004 |

OTHER PUBLICATIONS

"The Infusor" datasheet [online]. Baxter, Deerfield, IL [retrieved from the internet on Feb. 22, 2007]. Retrieved from the internet: <URL:http://www.baxter.com/products/medication_management/infusion_pumps/elastomeric_pumps/sub/infusor.html>; 1 pg.

U.S. Appl. No. 11/412,464, filed Apr. 27, 2006, Haase.

U.S. Appl. No. 11/412,592, filed Apr. 27, 2006, Haase.

U.S. Appl. No. 11/412,443, filed Apr. 27, 2006, Haase.

"Programmable Infusion System, The SynchroMed Pump" datasheet [online]. Medtronic, Inc., Minneapolis, MN, [retrieved on May 18, 2006]. Last updated Sep. 5, 2001. Retrieved from the Internet: <URL:http://www.medtronic.com/neuro/paintherapies/pain_treatment_ladder/drug_infusion/pumps_pump_sel/synchromed_pumps.html>; 6 pgs.

"SynchroMed Infusion System: Clinical Reference Guide for Pain Therapy" [online]. Medtronic, Inc., Minneapolis, MN, [retrieved on Oct. 4, 2006]. Retrieved from the Internet: <URL: http://www.medtronic.com/neuro/paintherapies/pain_treatment_ladder/pdf/1_reference_guide.pdf>; 81 pgs.

* cited by examiner

INFUSION DEVICE AND OVERFILL PROTECTION MECHANISM FOR USE WITH SAME

TECHNICAL FIELD

The present invention relates generally to medical devices and, more particularly, to infusion devices incorporating a system/mechanism for substantially reducing or eliminating overfilling of a reservoir of the device, and corresponding methods of using the same.

BACKGROUND

Treatment of diseases and ailments of the body often benefit from short- or long-term infusion of drugs and/or other fluids. While such therapeutic substances may be administered extracorporeally, e.g., via transcutaneous injection, many patient benefit from the consistent and repeatable dosage provided by an implantable infusion device. Such devices may be used in a variety of applications such as control of pain and/or spasticity. They are well-suited to deliver infusate fluids to a targeted delivery site such as an epidural or intrathecal space of the spinal canal, or a particular location within the brain.

Implantable infusion devices are typically implanted subcutaneously, e.g., in the chest or abdominal cavity. The device may incorporate a reservoir to hold the infusate fluid. A self-sealing, needle-penetrable septum may also be provided and is preferably located generally directly beneath the skin. The septum provides a refill port connected to a fluid passageway that permits the reservoir to be refilled periodically via transcutaneous injection. Accordingly, the reservoir can be aspirated and/or filled/refilled without requiring surgical removal from the patient's body, and further without requiring any other significant surgical procedure.

One potential problem with refilling the reservoir of some infusion devices is the potential for reservoir overfilling. Overfilling may lead to over-pressurization of the reservoir, which may cause damage to the components of the device and potentially result in other adverse consequences, e.g., over-infusion to the patient.

In some configurations, a clinician refilling the device with a syringe may rely upon tactile syringe resistance (e.g., pressure-based detection) to sense that the drug reservoir has been filled to capacity. While acceptable in some circumstances, inherent clinician variability may still result in over (or under)—filling. Moreover, while pressure-based systems are useful with some reservoir configurations (e.g., those using a bellows), such pressure-based solutions are not easily adaptable to devices incorporating flexible, ambient pressure reservoirs.

In other infusion devices, a pin may be mechanically coupled to a closed end of the reservoir such that a head of the pin seats to seal off the fluid passageway from the reservoir once the latter is at or near full capacity. While effective, devices incorporating such valve configurations may require a certain level of expertise to refill. For example, with the pin seated, aspiration of the reservoir may require the clinician to establish a sustained syringe vacuum pressure while the fluid slowly leaks around the pin and releases it from its valve seat.

Yet another potential problem with aspirating/refilling infusion devices concerns clinician feedback regarding needle position and fluid volume within the reservoir. For example, it may be difficult with some device configurations to determine whether the needle is fully and correctly located within the septum of the device. Accordingly, outside of tactile feedback detectable at the syringe, it may be difficult for less-experienced clinicians to initially determine whether the syringe fluid is being delivered into the reservoir or to an area outside of the device.

SUMMARY

The present invention may overcome these and other issues by providing, in one embodiment, an implantable infusion device including: a collapsible member defining a reservoir for containing a variable volume of fluid therein. The collapsible member includes a reservoir surface that moves between a full position and a refill position in response to a change in volume of the fluid contained in the reservoir. A housing is also provided and connected to the collapsible member. The housing includes a refill port for receiving the fluid, and a refill passageway connecting the refill port to the reservoir. The device also includes a valve plunger for selectively occluding the refill passageway, wherein the valve plunger comprises a free distal end configured to abut the reservoir surface of the collapsible member during movement between the full position and the refill position. A displacement sensor is also provided and coupled to the housing. The displacement sensor is operable to detect a position of the free distal end of the valve plunger as the reservoir surface moves from the full position to the refill position.

In another embodiment of the invention, a method for refilling fluid in an implantable infusion device is provided. The method includes connecting a transfer device to a refill port of the infusion device, wherein the infusion device further defines a reservoir and a refill passageway connecting the refill port to the reservoir. The method includes transporting the fluid from the transfer device along the refill passageway to the reservoir, wherein the reservoir is defined by a collapsible member that has a reservoir surface movable between a full position and a refill position in response to a change in volume of the fluid within the reservoir. The method also provides for biasing a valve plunger, which is positioned along the refill passageway, into contact with the reservoir surface; detecting a position of the valve plunger with a sensor; and closing the valve plunger to occlude the refill passageway when the reservoir surface reaches the full position.

In still yet another embodiment, an implantable infusion device is provided having a collapsible member defining a reservoir for containing a variable volume of fluid therein, wherein the collapsible member comprises a reservoir surface that moves between a full position and a refill position in response to a change in volume of the fluid contained in the reservoir. A housing is also provided and connected to the collapsible member. The housing defines: a refill port for receiving the fluid; and a refill passageway connecting the refill port to the reservoir. A valve plunger for selectively occluding the refill passageway is included, wherein the valve plunger comprises a free distal end configured to abut the reservoir surface of the collapsible member during movement between the full position and the refill position. The device further includes a displacement sensor at least partially positioned within the refill passageway. The sensor is operable to detect a position of the free distal end of the valve plunger as the reservoir surface moves from the full position to the refill position.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 4A-4C are partial section views of an exemplary infusion device (e.g., a device incorporating a pressurized bellows reservoir with a movable reservoir surface) incorporating an overfill protection mechanism in accordance with one exemplary embodiment of the invention, wherein: FIG. 4A illustrates the mechanism immediately prior to reaching a closed position; FIG. 4B illustrates a partial enlarged view of the mechanism in the closed position (corresponding to the reservoir surface being in a full position); and FIG. 4C illustrates the mechanism in a fully open position (corresponding to the reservoir surface being in a refill position)

The figures are rendered primarily for clarity and, as a result, are not necessarily drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the invention.

The present invention is directed to medical devices and, in particular, to implantable infusion devices and systems that are implanted within a patient's body. Infusion devices in accordance with embodiments of the present invention typically incorporate an overfill protection system or mechanism (OPM) to substantially reduce or eliminate overfilling and resulting over-pressurization of a reservoir of the device. The OPM may further incorporate a sensor that indicates a level of fluid, e.g., therapeutic substance, contained within the reservoir. Corresponding methods for filling/refilling fluid into the device, preventing reservoir overfill, and for detecting reservoir volume are also contemplated.

It is noted that the terms "comprises" and variations thereof do not have a limiting meaning where these terms appear in the accompanying description and claims. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

Figure 1:
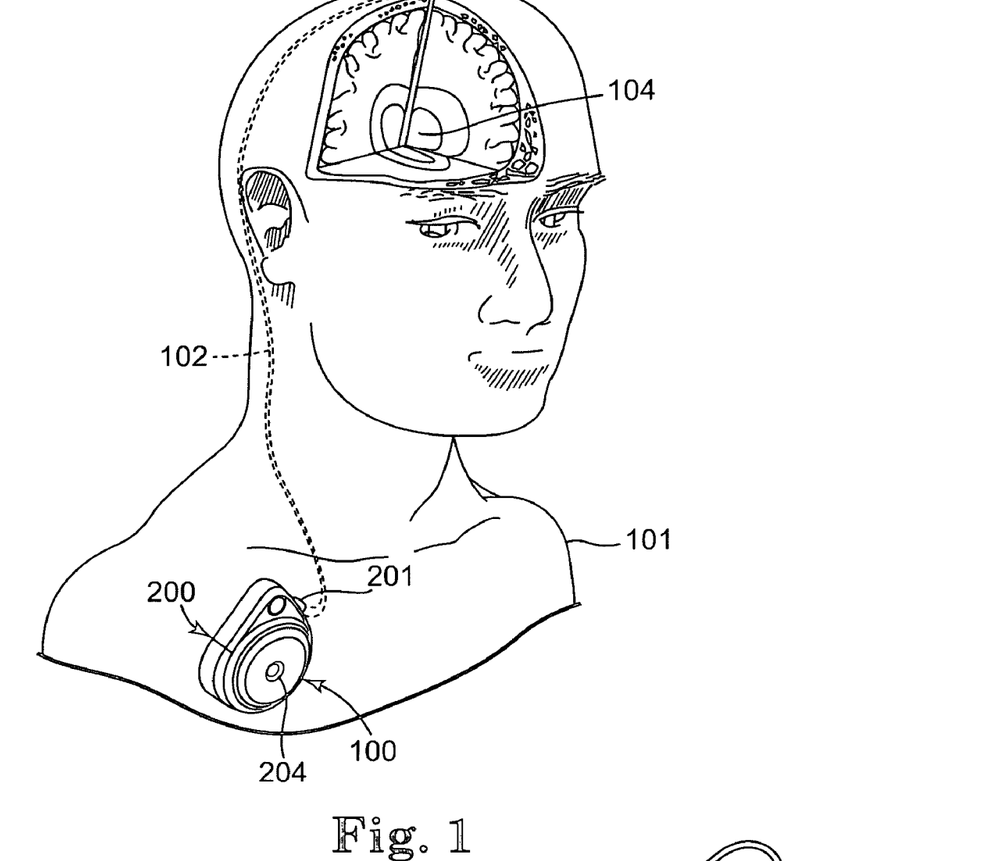
FIG. 1 illustrates an exemplary medical system, e.g., implantable infusion system, as it may be implanted in a patient's body, wherein the system incorporates an infusion device in accordance with one embodiment of the present invention.
Figure 2:
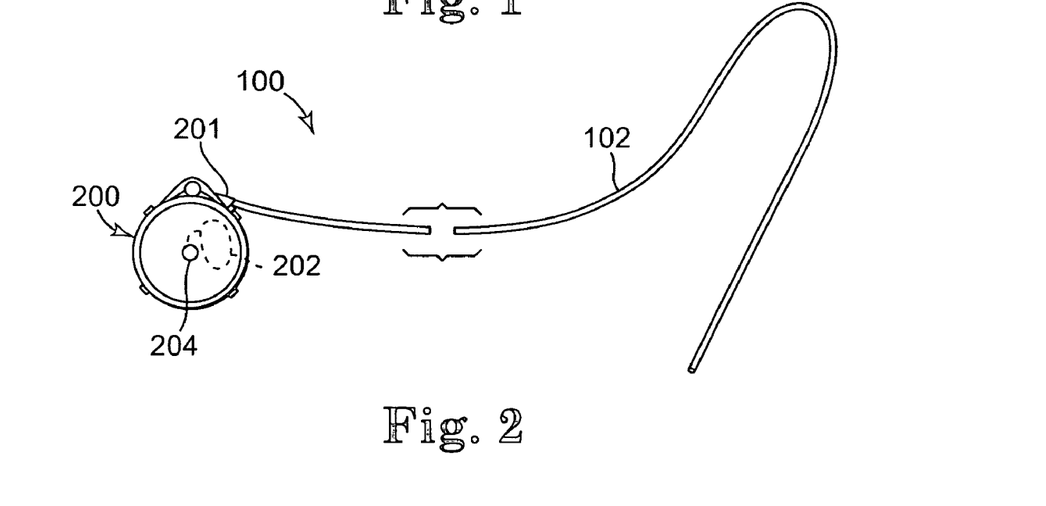
FIG. 2 is a view of the infusion system of FIG. 1 as removed from the body.

FIGS. 1 and 2 illustrate an implantable medical system, such as a therapeutic substance infusion system 100, in accordance with one embodiment of the invention (FIG. 1 illustrates the system 100 as it may be implanted within the patient's body 101, while FIG. 2 illustrates the system isolated, i.e., outside the body). The exemplary infusion system includes a medical device, e.g., implantable medical device 200, and at least one catheter 102. Such systems may be used for a wide variety of therapies including treatment of pain, spasticity, and other medical conditions.

The device 200 and catheter 102 are typically implanted by a clinician (e.g., surgeon) within the body 101 during a surgical procedure. While the present invention also contemplates embodiments wherein the catheter is implanted with one end outside the body so that it may attach to an external infusion device, the remainder of this description is, for the sake of brevity, directed to implantable medical systems.

Before implantation of the device 200, the catheter 102 may be positioned with its distal end (i.e., the end that does not couple to the device) located at a desired therapy delivery site 104 within the body 101, e.g., within the brain (while shown as delivering a therapeutic substance to a site 104 within the brain, the distal end of the catheter 102 may be located at most any location within the body 101, e.g., within an epidural or intrathecal space of the spinal canal). A proximal end of the catheter 102 may be tunneled through the tissue to the device implant location and coupled to a catheter or outlet port 201 of the device 200. The device 200 is typically implanted subcutaneously, e.g., about 2.5 centimeters (cm) (1 inch (in)) beneath the skin, where there is sufficient tissue for supporting the device, e.g., with sutures or the like.

The device 200 is, in the illustrated embodiment, operable to infuse a therapeutic substance (also referred to as "fluid" or "drug" herein) from an enclosed reservoir 202 (illustrated in more detail in FIGS. 4A-4C and 5) into the body 101. The "therapeutic substance" may be a product or substance intended to have a therapeutic effect on the patient, e.g., pharmaceutical compositions, genetic materials, biologics, and other substances.

"Pharmaceutical compositions," as used herein, may include chemical formulations intended to have a therapeutic effect such as intrathecal antispasmodics, pain medications, chemotherapeutic agents, and the like. Pharmaceutical compositions are often configured to function effectively in an implanted environment by possessing various characteristics including: stability at body temperature to retain therapeutic qualities; concentration to reduce the frequency of replenishment; and the like. "Genetic materials," as used herein, may include substances intended to have a direct or indirect genetic therapeutic effect such as genetic vectors, genetic regulator elements, genetic structural elements, DNA, and the like. "Biologics," as used herein, may include substances that are living matter, or derived from living matter, and offer a therapeutic effect to the patient such as stem cells, platelets, hormones, biologically produced chemicals, and the like. "Other substances" may include most any other substance that is intended to have a therapeutic effect, yet does not clearly fit within one of the categories identified above. Examples of other substances may include saline solutions, fluoroscopy agents, and the like.

In some embodiments, the therapeutic substance contained within the reservoir 202 may be replenished periodically after device implantation. Typically, replenishment is accomplished with a non-coring needle (not shown) connected to a syringe filled with the therapeutic substance. The needle may be inserted through the patient's skin and into a self-sealing septum 204 of the device 200.

Figure 3:
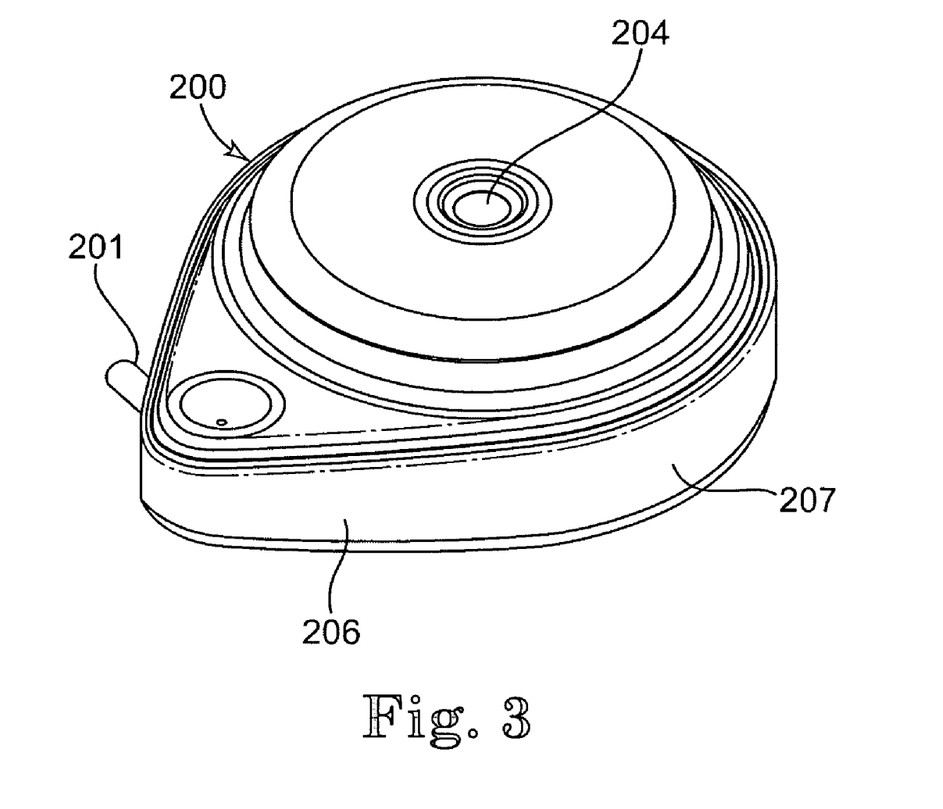
FIG. 3 is an enlarged perspective view of an exemplary infusion device such as that illustrated in the system of FIGS. 1 and 2.

FIG. 3 illustrates an exemplary embodiment of the device 200. As shown in this view, the device 200 may include a housing 207 which encloses some or all of the various components (including, for example, a power source (e.g., battery), electronics, and a metering mechanism) of the device. The exemplary reservoir 202 may be a variable volume reservoir, e.g., a reservoir capable of holding a variable volume of fluid therein. In this embodiment, the reservoir 202 is fully contained within, and surrounded by, the housing 207 so that a contained propellant may be used to pressurize the reservoir. However, reservoirs having other variable volume configurations, e.g., an exposed flexible polymeric pouch, are certainly possible without departing from the scope of the invention.

Figures 4A, 4B:
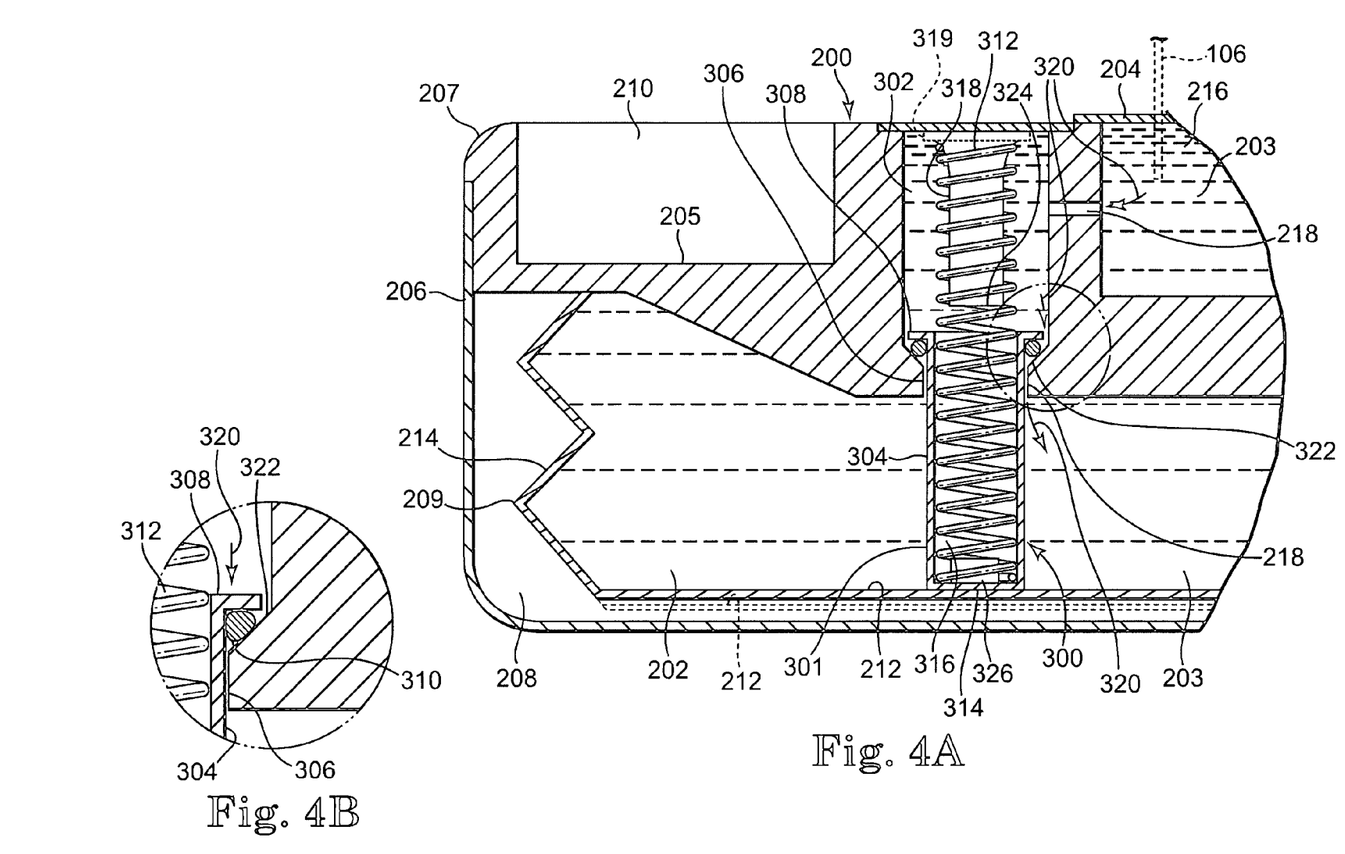
Figure 4C:
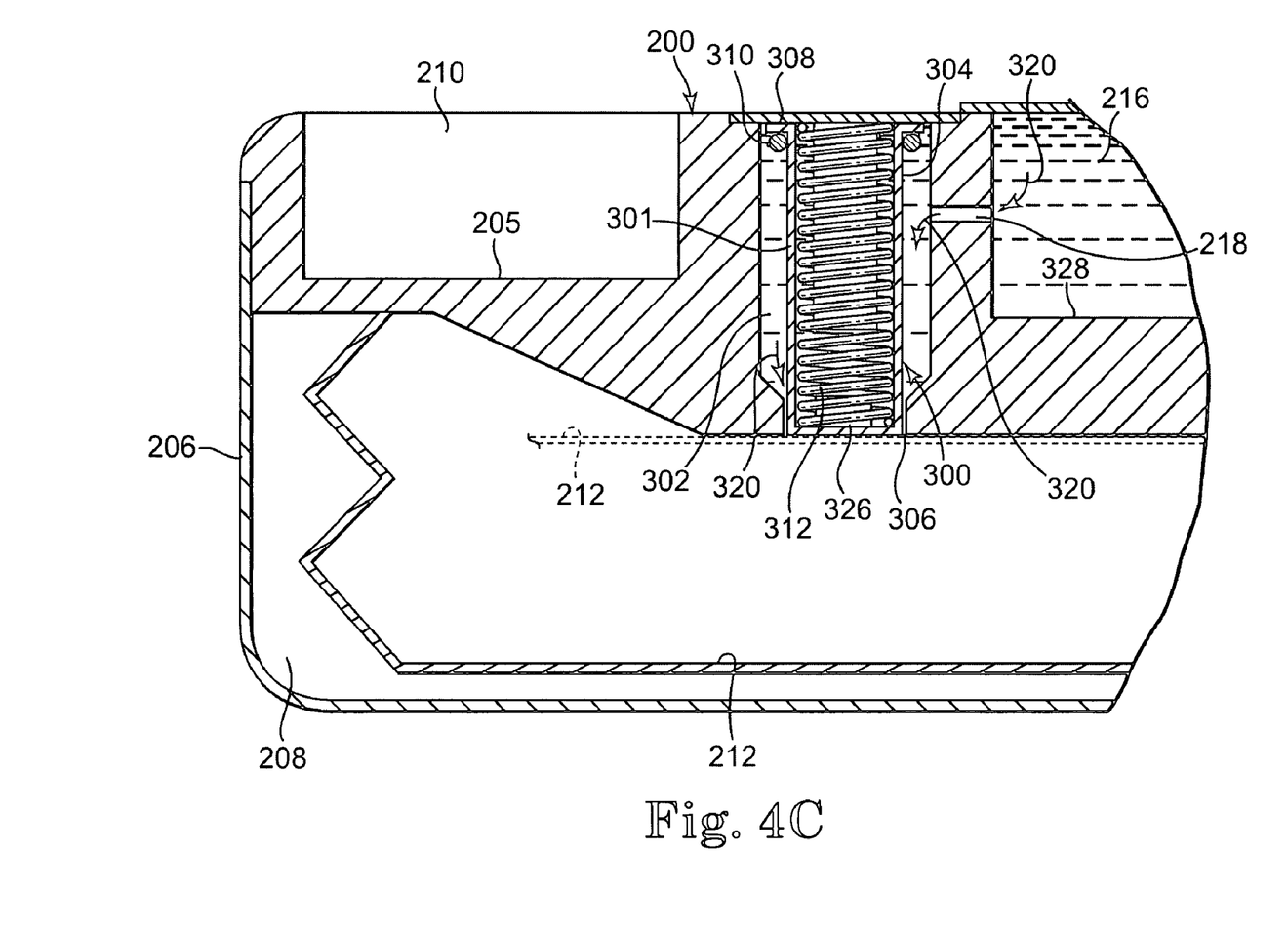

FIGS. 4A-4C illustrate partial cross sections of the device 200. As with the remaining figures, some features/aspects of the device that are not central to an understanding of the invention may not be shown or may be represented diagrammatically.

The housing 207 may include both a bulkhead 205 that effectively isolates the reservoir 202 from other portions (e.g., electronics 210) of the device 200, and an enclosure 206. The housing 207 may also include most any other part that is used to retain, support, or enclose the components of the device 200. Some exemplary components that may be secured in the housing (e.g., to the bulkhead) include the power source (not shown), metering mechanism (e.g., a pump (also not shown)), and other powered components. Alternative housings, e.g., those lacking the enclosure 206, are also possible without departing from the scope of the invention.

The electronics 210 are preferably configured to control at least the infusion rate of the pump (where included), and may also be configured to operate separate device features such as patient alarms and the like. The electronics 210 may further connect to, or otherwise incorporate, telemetry circuitry to receive and send information regarding the device 200, and to permit remote programming of device characteristics, e.g., the infusion rate, by the clinician. As further described below, the electronics may also connect to a sensor operable to detect the volume of fluid contained in the reservoir 202.

As illustrated in FIG. 4A, the reservoir 202 may, in one embodiment, be defined by a collapsible member, e.g., a bellows 209, having a movable reservoir surface 212 connected and sealed to the bulkhead 205 via an accordion-like, collapsible cylindrical wall 214. The reservoir surface 212 may move (upwardly and downwardly in FIG. 4A) in response to a change in volume of the fluid contained in the reservoir 202.

The reservoir 202 may be in fluid communication with a refill port 216 (covered by the septum 204) via a refill passageway 218. The refill port 216 and refill passageway 218 may be formed or defined in the housing 207, e.g., within the bulkhead 205. The port 216 may be used to remove and/or receive fluid (e.g., therapeutic substance 203) for aspiration and/or replenishment of the reservoir 202 via transcutaneous injection. Although not illustrated in FIG. 4A, the reservoir 202 may further be in fluid communication with the outlet port 201 (see FIGS. 2 and 3) via a fluid or delivery passageway (not shown) for delivering the therapeutic substance 203 to the body 101 (see FIG. 1).

A propellant chamber 208 may surround the reservoir, e.g., in the annular space between the bellows and the enclosure 206. The propellant chamber 208 may contain a propellant at a pressure the same as, or different than, ambient pressure, e.g., at a relative positive or negative pressure.

The device 200 may further include an OPM 300 situated between the refill port 216 and the reservoir 202, i.e., along or within the refill passageway 218. In one embodiment, the OPM 300 is positioned within a transfer chamber 302 that forms a portion of the refill passageway 218 and is, therefore, fluidly coupled to both the refill port 216 and the reservoir 202. The OPM 300 may include a telescoping valve plunger 301 having a cylindrical valve body 304 slidable within a valve passageway 306 formed in the bulkhead 205. A clearance preferably exists between a diameter of the valve body 304 and the valve passageway 306 so that fluid, e.g., therapeutic substance 203, may flow between the transfer chamber 302 and the reservoir 202 during the refill process. In one embodiment, the valve body 304, e.g., valve plunger 301, defines an axis (e.g., a longitudinal axis along which the valve moves) that is parallel to, and offset from, an axis of the refill port 216.

A cylindrical flanged portion or head 308 may be formed at a first, e.g., upper, end of the valve body 304. The head 308 has an outer diameter larger than the diameter of the valve body 304 and the valve passageway 306 as shown in FIGS. 4A and 4B. A sealing member, e.g., O-ring 310, may be located on the valve body 304 proximate the head 308. The O-ring 310 may permit selective sealing of the refill passageway 218, e.g., sealing of the valve passageway 306, as further described below.

The OPM 300 may further include a biasing member, e.g., coil spring 312, positioned to contact the valve plunger and bias it into contact with the reservoir surface 212. That is, the spring 312 may bias a free distal end 314 of the valve plunger 301 to abut the reservoir surface 212 of the collapsible member during movement between a full position and a refill position. In one embodiment, the valve is open at a proximal end and closed at its distal end such that it defines an internal barrel-shaped space 316 operable to receive and contain a distal end of the spring 312. A proximal end of the spring 312 may slide over a guide member 318 extending into the transfer chamber 302 from a reaction surface of the housing 207 as shown in FIG. 4A. By providing the guide member 318 and guiding space 316, the spring 312 may be constrained against lateral movement over all, or substantially all, of the valve plunger's travel.

While illustrated as relatively flat, the distal end 314 of the valve body 304 may have alternative shapes, e.g., rounded, to reduce side loading of the valve plunger 301. Moreover, the distal end 314 could include a bearing member (not shown) of a material the same as or different than a material of one or both of the valve plunger 301 and the reservoir surface 212. The bearing member may be positioned between the distal end 314 of the valve plunger and the reservoir surface 212. Exemplary materials from which the valve plunger 301 may be constructed include titanium, polytetrafluoroethylene (PTFE), and polysulfone. Exemplary materials from which a bearing member could be constructed include titanium, silicone, and PTFE.

FIG. 4A illustrates the OPM 300 with the valve plunger 301 in a position prior to the reservoir surface 212 (and reservoir 202) reaching the full position (the full position of the reservoir surface is shown in broken lines in FIG. 4A). As shown by arrows 320, when the valve plunger 301 is in this position (or any other open position), therapeutic substance 203 may flow from the transfer chamber 302 into the reservoir 202. However, when the reservoir surface 212 reaches the full position, the valve plunger 301 (e.g., the head 308) closes and compresses the seal 310 again a valve seat 322 as shown in FIG. 4B, thereby selectively occluding the refill passageway 218 such that flow of therapeutic substance 203 into the reservoir is terminated.

The OPM 300 may further include a displacement or level sensor that may be coupled to the housing and operable to detect the volume of fluid contained in the reservoir 202. The displacement sensor may, in one embodiment, be an inductive proximity sensor 324 positioned on, or in place of, the spring guide 318, e.g., positioned at a fixed location within the refill passageway 218. The sensor 324 may be electrically coupled to the electronics 210 and power source (not shown). A sensor target, e.g., a magnet 326, may be attached to the valve plunger 301 (e.g., hermetically sealed and attached at or near the free distal end 314) such that the particular position of the valve is detectable by the sensor 324. Stated alternatively, the sensor 324 may detect a position of the free distal end 314 of the valve plunger 301 relative to a fixed location within the housing as the reservoir surface moves from the full position to the refill position. While illustrated herein as an inductive proximity sensor, most any other type of position or proximity sensor or transducer, e.g., linear variable differential transformer (LVDT), may be used without departing from the scope of the invention. Alternatively, instead of direct displacement devices, the sensor could include a load sensing device, e.g., a load cell 319 as shown in FIG. 4A, which could detect plunger position based upon actual spring load.

With reference to FIGS. 4A-4C, an exemplary method of refilling fluid in an implantable medical device using the device 200 and OPM 300 is described below. A transfer device, such as needle 106, may be connected to, e.g., inserted into, the refill port via the septum 204. A needle stop surface 328 may be formed at one end of the refill port 216 to limit needle insertion. Where aspiration is desired, the clinician may draw a syringe vacuum via the needle. Once the force applied by syringe vacuum pressure (applied over the relatively large diameter of the head 308) exceeds the spring force, the valve plunger 301 may open and therapeutic substance 203 may be withdrawn from the reservoir 202.

Advantageously, the relatively large area of the head 308 of the valve plunger 301 may permit the clinician to open the valve plunger without having to apply a large force to the syringe plunger as may be the case with a pin valve having a smaller head size. Moreover, because the valve plunger 301 is not physically attached to the reservoir surface 212, the syringe vacuum pressure required to open the valve is not affected by the force exerted on the reservoir surface 212 by either elevated internal reservoir pressure or external vacuum pressure (from within the propellant chamber 208). For example, in negative pressure devices where the reservoir surface 212 is in the full position (broken line rendering in FIG. 4A), the larger area of the head 308 may permit opening of the valve plunger 301 via the application of a relatively small syringe plunger force. This feature is attributable, at least in part, to the ability of the plunger to pull away from the reservoir surface 212 when syringe vacuum is applied. This is especially beneficial when, for example, air is trapped in the reservoir.

The diameters of the valve body 304 and head 308, and the spring force, may be varied to control the actual force required to open the valve plunger 301. For example, in one embodiment, the valve head is about 5 cm (0.20 in) in diameter. Using a spring 312 that has a spring force of about 0.05 pounds-force in the extended position, the valve plunger 301 may be opened with the application of a syringe vacuum pressure of about 1.6 pounds per square inch (psi) less than the reservoir pressure.

Once the valve plunger 301 is open, the therapeutic substance 203 may be withdrawn via the needle 106 inserted into the refill port 216. During aspiration, the clinician may monitor the fluid level of the reservoir 202 as provided by the sensor 324 to ensure that the needle is properly inserted into the refill port and that fluid is being withdrawn. When the reservoir 202 is completely aspirated, the reservoir surface 212 may be located proximate to, or in contact with, the bulkhead 205 as shown in broken lines in FIG. 4C. Due to the biasing contact of the valve plunger 301 with the reservoir surface 212, the valve body 304 remains in contact with the reservoir surface 212 throughout its movement. As a result, accurate reservoir volume measurements may be obtained from the sensor 324 and transmitted outside the body (e.g., via the device's telemetry circuitry) to the clinician.

The syringe flow may be reversed for reservoir refilling. Accordingly, therapeutic substance 203 may be injected, via the needle 106, into the refill port 216. The fluid substance is then transported along the refill passageway 218, into the transfer chamber 302, and to the reservoir 202 as indicated by arrows 320 in FIGS. 4A and 4C. The reservoir surface 212 may move from the refill position illustrated in broken lines in FIG. 4C, towards the full position illustrated in broken lines in FIG. 4A in response to a change in the volume of fluid contained in the reservoir. The spring 312 ensures that the valve plunger 301 is biased into contact with the reservoir surface such that it moves in unison with the reservoir surface. Moreover, the sensor 324 output assures the clinician that the fluid is entering the reservoir 202 as expected.

As the reservoir approaches the full position (see broken line representation in FIG. 4A), the valve head 308 approaches the valve seat 322. The length of valve body 304 from the head 308 to the distal end 314 may be selected such that the seal 310 engages the valve seat 322 (as illustrated in FIG. 4B) at the same time that the reservoir surface 212 reaches the full position (shown in broken lines in FIG. 4A). As a result, the OPM 300 may close before overfilling of the reservoir 202 occurs. The clinician may detect the closing of the OPM 300 via the tactile feedback at the refill syringe, or via the sensor 324 (e.g., the sensor may indicate a full position, or the sensor may merely indicate that filling has stopped).

Figure 5:
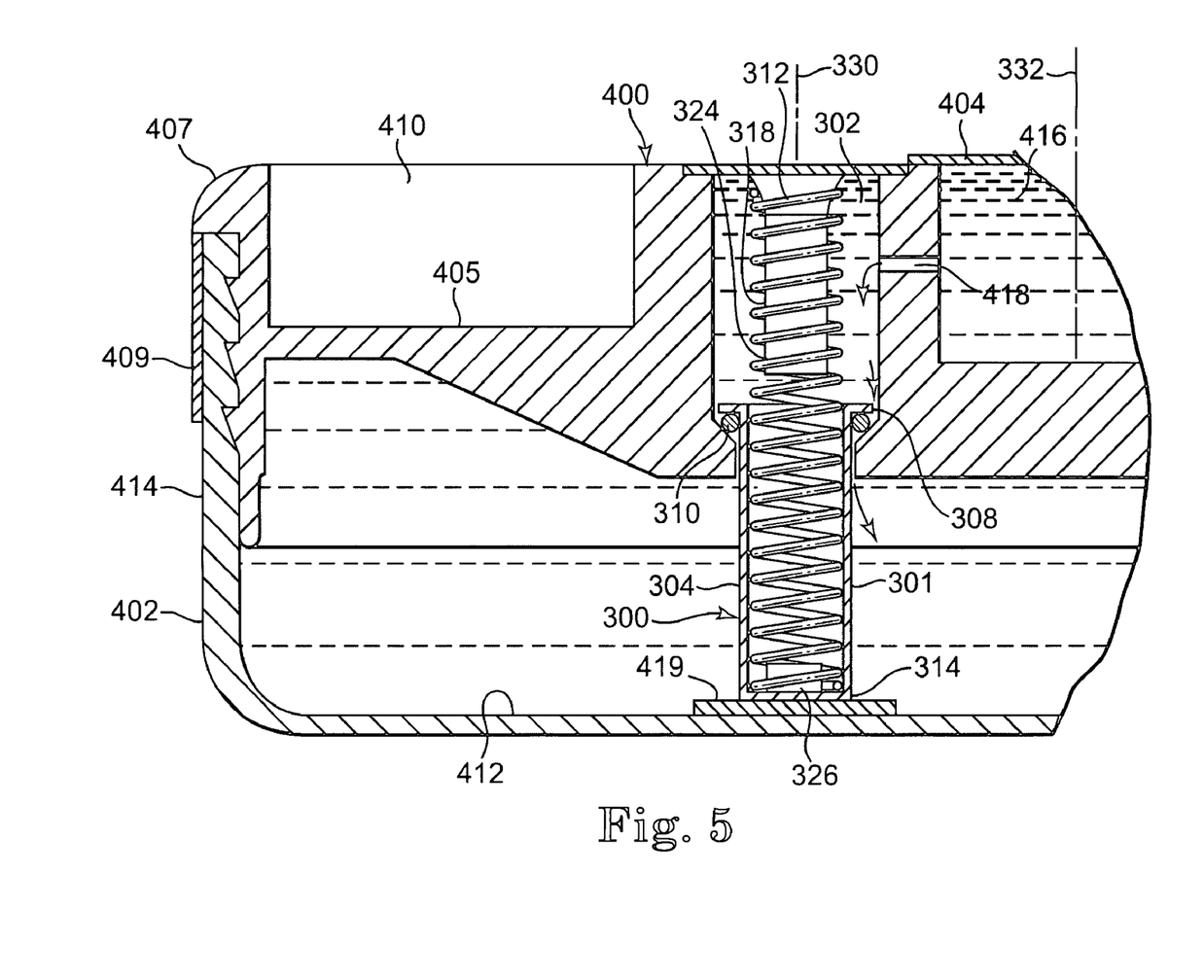
FIG. 5 illustrates a partial section view of another infusion device (e.g., a device incorporating a flexible, ambient pressure reservoir) incorporating an overfill protection mechanism in accordance with another embodiment of the invention.

Advantageously, the displacement-based operation of the OPM 300 is well suited to both bellows and flexible bladder-type reservoirs. FIG. 5 illustrates an alternative embodiment of the invention, wherein the OPM 300 is included with an infusion device 400 having a collapsible member formed by a flexible, ambient pressure reservoir 402. As the OPM 300 itself is described in detail above, no further description is provided below.

Many components of the device 400 are substantially identical to the components of the device 200 already described above (unless otherwise indicated herein). For example, the device includes an outlet port (similar to the outlet port 201 described above), as well as a septum 404 and refill port 416 connected via a refill passageway 418 to the reservoir 402. A housing 407 including a bulkhead 405 is also provided. As the device 400 is designed to operate at ambient pressure, it is not necessary to include an enclosure like that of the device 200. The device 400 may further include electronics 410, pump (not shown) and a power source (also not shown). As a result of these similarities, the device 400 may operate in substantially the same manner as the device 200 already described above (except, of course, without the use of a propellant).

The collapsible member, in the embodiment of FIG. 5, is preferably a flexible polymeric pouch that can withstand the anticipated pressure differentials and that is sufficiently flexible to permit expansion and contraction as the reservoir volume changes. The material of the reservoir may also have self-sealing characteristics in case of accidental puncture during the replenishment process. Exemplary materials for the reservoir include silicone and polyurethane.

The pouch may include a flexible reservoir surface 412 connected to the bulkhead 405 via a flexible cylindrical wall 414. The wall 414 may attach to the bulkhead via one or more barbs. In addition, or alternatively, a clamp member 409 may be provided to secure the reservoir 402 to the bulkhead 405.

As the reservoir 402 is depleted, it may collapse, causing the reservoir surface 412 to move towards the bulkhead 405 in a manner substantially similar to the reservoir surface 212 already described herein. As the valve plunger 301 moves in unison with the surface 412, reservoir fluid level may be detected with the sensor 324 as already described herein.

In one embodiment, a bearing member 419 may be provided and positioned between the distal end 314 of the valve body 304 and the reservoir surface 412. The bearing member 419 may assist in distributing the biasing load of the valve plunger 301 to avoid overstressing a localized area of the reservoir surface 412. The bearing member 419 may be attached to either the distal end 314 of the valve plunger 301, or to the reservoir surface 412.

OPMs and medical devices incorporating OPMs in accordance with embodiments of the present invention may substantially reduce or eliminate inadvertent overfilling of the device reservoir by providing a displacement-based valve for selectively occluding the refill passageway prior to the reservoir reaching an overfill status. Moreover, OPMs in accordance with embodiments of the present invention may provide a valve having a relatively large valve head. The head size is beneficial in that it permits opening of the valve plunger 301 at relatively low syringe vacuum pressures to permit aspiration of the reservoir. A displacement sensor may also be included with OPM embodiments described and illustrated herein. The displacement sensor provides the clinician with feedback regarding accurate needle placement, as well as feedback regarding the volume of fluid in the reservoir at any time during the aspiration/refill process or during therapy via telemetry.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An implantable infusion device, comprising:
    a collapsible member defining a reservoir for containing a variable volume of fluid therein, wherein the collapsible member comprises a reservoir surface that moves between a full position and a refill position in response to a change in volume of the fluid contained in the reservoir;
    a housing connected to the collapsible member, the housing defining: a refill port for receiving the fluid; and a refill passageway connecting the refill port to the reservoir;
    a valve plunger for selectively occluding the refill passageway, wherein the valve plunger comprises a free distal end configured to abut the reservoir surface of the collapsible member during movement between the full position and the refill position; and
    a displacement sensor coupled to the housing and operable to detect a position of the free distal end of the valve plunger at any time during movement of the reservoir surface between the full position and the refill position, the displacement sensor electrically coupled to electronics configured to provide feedback corresponding to the detected position of the free distal end.

2. The device of claim 1, further comprising a biasing member positioned in contact with the valve plunger, the biasing member to bias the free distal end of the valve plunger into contact with the reservoir surface.

3. The device of claim 2, wherein the biasing member extends between the valve plunger and a reaction surface of the housing.

4. The device of claim 3, further comprising a guide member extending from the reaction surface to guide the biasing member.

5. The device of claim 2, wherein the biasing member is a coil spring.

6. The device of claim 1, wherein the valve plunger or the reservoir surface further comprises a bearing member positioned between the free distal end of the valve plunger and the reservoir surface.

7. The device of claim 6, wherein the bearing member comprises a material different than a material of one or both of the valve plunger and the reservoir surface.

8. The device of claim 6, wherein the bearing member is attached to the distal end of the valve plunger.

9. The device of claim 6, wherein the bearing member is attached to the reservoir surface.

10. The device of claim 1, wherein the valve plunger defines an axis that is parallel to, and offset from, an axis of the refill port.

11. The device of claim 1, wherein the displacement sensor comprises an inductive proximity sensor.

12. The device of claim 1, further comprising a magnet coupled at or near the free distal end of the valve plunger.

13. The device of claim 1, wherein the displacement sensor comprises a load cell.

14. The device of claim 1, wherein the collapsible member comprises a polymeric pouch.

15. The device of claim 1, wherein the collapsible member comprises a bellows.

16. A method for refilling fluid in an implantable infusion device, the method comprising:
    connecting a transfer device to a refill port of the infusion device, the infusion device defining a reservoir and a refill passageway connecting the refill port to the reservoir;
    transporting the fluid from the transfer device along the refill passageway to the reservoir, wherein the reservoir is defined by a collapsible member that comprises a reservoir surface movable between a full position and a refill position in response to a change in volume of the fluid within the reservoir;
    biasing a valve plunger, which is positioned along the refill passageway, into contact with the reservoir surface;
    detecting a position of the valve plunger with a sensor at any time during movement of the reservoir surface between the full position and the refill position, the sensor electrically coupled to electronics configured to provide feedback corresponding to the detected position of the valve plunger; and closing the valve plunger to occlude the refill passageway when the reservoir surface reaches the full position.

17. The method of claim 16, wherein detecting the position of the valve plunger comprises determining a location of a free distal tip of the valve plunger relative to a fixed location within a housing of the device.

18. The method of claim 16, wherein connecting the transfer device to the inlet port comprises inserting a needle into a self-sealing septum of the device.

19. An implantable infusion device, comprising:
a collapsible member defining a reservoir for containing a variable volume of fluid therein, wherein the collapsible member comprises a reservoir surface that moves between a full position and a refill position in response to a change in volume of the fluid contained in the reservoir;
a housing connected to the collapsible member, the housing defining: a refill port for receiving the fluid; and a refill passageway connecting the refill port to the reservoir;
a valve plunger for selectively occluding the refill passageway, wherein the valve plunger comprises a free distal end configured to abut the reservoir surface of the collapsible member during movement between the full position and the refill position; and
a displacement sensor at least partially positioned within the refill passageway, the sensor operable to detect a position of the free distal end of the valve plunger at any time during movement of the reservoir surface between the full position and the refill position, the displacement sensor electrically coupled to electronics configured to provide feedback corresponding to the detected position of the free distal end.

20. The device of claim 19, wherein the collapsible member comprises a polymeric pouch.

21. The device of claim 19, wherein the collapsible member comprises a bellows.

22. The device of claim 19, further comprising an enclosure surrounding the collapsible member, the enclosure defining a propellant chamber operable to pressurize the reservoir.

23. The device of claim 19, wherein the displacement sensor comprises an inductive proximity sensor, and a sensor target positioned at or near the free distal end of the valve plunger.

24. The device of claim 19, further comprising a biasing member to bias the free distal end of the valve plunger towards the reservoir surface.

25. The device of claim 19, wherein the displacement sensor comprises a load cell.

* * * * *